United States Patent
Abunassar et al.

(10) Patent No.: US 9,918,822 B2
(45) Date of Patent: Mar. 20, 2018

(54) SYSTEM AND METHOD FOR RENAL NEUROMODULATION BY OVERSIZED STENT

(71) Applicant: ABBOTT CARDIOVASCULAR SYSTEMS INC., Santa Clara, CA (US)

(72) Inventors: Chad Abunassar, San Francisco, CA (US); Erik D. Eli, Redwood City, CA (US); Denis Tauz, Los Gatos, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 285 days.

(21) Appl. No.: 14/918,191

(22) Filed: Oct. 20, 2015

(65) Prior Publication Data

US 2017/0106177 A1   Apr. 20, 2017

(51) Int. Cl.
*A61F 2/06* (2013.01)
*A61F 2/91* (2013.01)

(52) U.S. Cl.
CPC ............... *A61F 2/06* (2013.01); *A61F 2/91* (2013.01); *A61F 2210/0004* (2013.01); *A61F 2230/0069* (2013.01); *A61F 2250/0036* (2013.01); *A61F 2250/0071* (2013.01)

(58) Field of Classification Search
CPC ............ A61B 18/1492; A61B 18/14; A61B 2018/00267; A61B 2018/00404; A61B 2018/00434; A61B 2018/00214; A61B 2018/00511; A61B 2018/00577; A61B 17/11; A61B 2017/22002; A61F 2/90; A61F 2/88; A61F 2/82; A61F 2/95; A61F 2210/0004; A61F 2230/0078; A61F 2250/0001; A61M 25/0084; A61M 25/1002; A61M 25/1011; A61M 25/04; A61M 2025/1047; A61L 31/148; A61L 2300/416; A61N 1/36007; A61N 1/0551; A61N 1/327

See application file for complete search history.

(56) References Cited

U.S. PATENT DOCUMENTS

| | | | |
|---|---|---|---|
| 5,722,401 | A | 3/1998 | Pietroski et al. |
| 6,155,264 | A | 12/2000 | Ressemann et al. |
| 6,238,421 | B1 | 5/2001 | Gunther et al. |
| 6,293,955 | B1 | 9/2001 | Houser et al. |
| 6,475,233 | B2 | 11/2002 | Trozera |

(Continued)

*Primary Examiner* — Jonathan Miles
*Assistant Examiner* — Mohamed Gabr
(74) *Attorney, Agent, or Firm* — David J. Pitman; Fulwider Patton LLP

(57) ABSTRACT

A method of stimulating a renal nerve in a human patient comprising, selecting a span of renal artery in the patient for implantation of a self-expanding stent, the artery having a first internal diameter, an artery wall, and being surrounded by peri-adventitial space through which at least one renal nerve extends; measuring the first internal diameter; selecting a self-expanding stent configured to be capable of expanding to have a second diameter that, in an expanded condition once implanted within the artery, is between 2 mm and 4 mm larger than the first diameter; implanting the stent in the span of the renal artery, whereby the stent eventually expands to the second diameter and thereby passes through the artery wall to become embedded in peri-advential space; and at least partially blocking the renal nerve or modulating a function of the nerve.

12 Claims, 5 Drawing Sheets

(56) References Cited

U.S. PATENT DOCUMENTS

| | | |
|---|---|---|
| 6,542,781 B1 | 4/2003 | Koblish et al. |
| 6,623,452 B2 | 9/2003 | Chien et al. |
| 6,802,857 B1 | 10/2004 | Walsh et al. |
| 7,708,715 B2 | 5/2010 | Gellman |
| 7,918,883 B2 | 4/2011 | Weber |
| 7,972,371 B2 | 7/2011 | Martin |
| 8,043,257 B2 | 10/2011 | Nguyen et al. |
| 8,131,371 B2 | 3/2012 | Demarals et al. |
| 8,412,346 B2 | 4/2013 | Gellman et al. |
| 8,473,067 B2 | 6/2013 | Hastings et al. |
| 2004/0138738 A1 | 7/2004 | Stinson |
| 2005/0059931 A1 | 3/2005 | Garrison et al. |
| 2009/0093791 A1 | 4/2009 | Heuser |
| 2009/0182404 A1 | 7/2009 | Shokoohi |
| 2011/0182912 A1* | 7/2011 | Evans ............... A61M 25/0084 424/158.1 |
| 2012/0150282 A1 | 6/2012 | Adden et al. |
| 2013/0245621 A1 | 9/2013 | Persson et al. |
| 2014/0343590 A1* | 11/2014 | Solem ................... A61B 17/32 606/185 |

\* cited by examiner

SYSTEM AND METHOD FOR RENAL NEUROMODULATION BY OVERSIZED STENT

BACKGROUND

This invention relates to methods and devices for treatment of diseases that include congestive heart failure, chronic renal failure and hypertension. Specifically, the invention relates to improving conditions in patients by blocking or at least modifying (modulating) signals via the renal nerve.

Heart Failure

Congestive Heart Failure (CHF) is a form of heart disease that is becoming ever more common. The number of patients with CHF is expected to grow in increasing numbers as the so-called "Baby Boomers" reach 50 years of age. CHF is a health condition that occurs when the heart becomes damaged, resulting in a reduced blood flow to the organs of the body. If blood flow decreases sufficiently, kidney function becomes impaired and results in fluid retention, abnormal hormone secretions and increased constriction of blood vessels. These results increase the stress on the heart to do work, and further decrease the capacity of the heart to pump blood through the kidney and vascular circulation system. This reduced capacity further reduces blood flow to the kidney. It is believed that this cycle of reduced kidney perfusion is the principal non-cardiac cause perpetuating a patient's downward spiral into CHF. Moreover, the fluid overload and associated clinical symptoms resulting from these changes are predominant causes for excessive hospital admissions, reduced quality of life and overwhelming costs to the health care system.

While many different diseases may cause initial damage to the heart, once such damage is present, CHF is identifiable under two types: Chronic CHF and Acute CHF. Despite its name, the chronic form is the less acute form of the two but is a longer term, slowly progressive, degenerative disease, and may lead to cardiac insufficiency. Chronic CHF is clinically categorized by the patient's mere inability to exercise or perform normal activities of daily living.

By contrast, patients with Acute CHF may experience a more severe deterioration in heart function than those with Chronic CHF. The Acute form results in the inability of the heart to maintain sufficient blood flow and pressure to keep vital organs of the body alive. This condition can occur when extra stress (such as by infection) significantly increases the workload on the heart in a patient with an otherwise stable form of CHF. By contrast to a mere stepwise downward progression that is observable in patients with Chronic CHF, a patient suffering Acute CHF may deteriorate rapidly from even the earliest stages of CHF to severe hemodynamic collapse. Moreover, Acute CHF can occur within hours or days following an Acute Myocardial Infarction (AMI), which is a sudden, irreversible injury to the heart muscle, identified in common parlance as a heart attack.

Kidney Failure

Against this background, the kidneys are known to play an important regulatory role in maintaining the homeostatic balance of the body. The kidneys eliminate foreign chemicals from the body, regulate inorganic substances, and function as endocrine glands to secrete hormonal substances like renin and erythropoietin. The main functions of the kidney are to maintain the water balance of the body and control metabolic homeostasis by making the urine more or less concentrated, thus either reabsorbing or excreting more fluid. However, when renal disease arises, some otherwise ordinary and regular physiological functions may become detrimental to the patient's health. When this occurs, the process is known as overcompensation. In the case of Chronic Renal Failure (CRF) the event of overcompensation may manifest itself as hypertension that has the effect of damaging the heart and blood vessels, and can eventually result in a stroke or death. Thus, without proper function by the kidneys, a patient may suffer water retention, reduced urine flow and an accumulation of waste toxins in the blood and body. These conditions resulting from reduced renal function, or renal failure (kidney failure), tend to increase the workload placed upon the heart. In a patient, simultaneous occurrence of both CRF and CHF may cause the heart to further deteriorate as the water build-up and blood toxins accumulate due to the poorly functioning kidneys and may, in turn, cause the heart further harm.

Nervous System

It has been observed, in connection with human kidney transplantation, that there is evidence to suggest that the nervous system plays a major role in kidney function. It was noted for example that after a transplant, when all the renal nerves are severed, the kidney was observed to increase excretion of water and sodium. This phenomenon has also been observed in animals when renal nerves are cut or chemically destroyed. The phenomenon has been termed "denervation diuresis" because the denervation acted on a kidney in a similar way to a diuretic medication. Later, observation of "denervation diuresis" was found to be associated with the vasodilatation of the renal arterial system that led to the increase of the blood flow through the kidney. This observation was confirmed by the observation in animals that reducing blood pressure supplying the kidney could reverse the "denervation diuresis".

It was also observed that after several months passed after the transplant surgery in successful cases, the "denervation diuresis" in transplant recipients stopped, and the kidney function returned to normal. Initially, it was believed that "renal diuresis" is merely a passing phenomenon and that the nerves conducting signals from the central nervous system to the kidney are not essential for kidney function. Later discoveries led to the present generally held conclusion that the renal nerves have an ability to regenerate, and that the reversal of the "denervation diuresis" is attributable to the growth of the new nerve fibers supplying kidneys with the necessary stimuli.

In summary then, it is known from clinical experience and also from the large body of animal research that stimulation of the renal nerve leads to the vasoconstriction of blood vessels supplying the kidney, decreased renal blood flow, decreased removal of water and sodium from the body and increased renin secretion. It is also known that reduction of the sympathetic renal nerve activity, achieved by denervation, can reverse these processes.

Steps Taken in the Prior Art, and Problems Arising

There has therefore already been identified a need in the art for methods and devices that may apply the observed effects set forth above to halt and reverse the symptoms of Congestive Heart Failure. Thus, certain methods and devices have already been commercialized in the art to reduce renal nerve activity, in order to meet the aforesaid need. For example, the following patents are directed to the stated need: U.S. Pat. No. 7,620,451, U.S. Pat. No. 6,978,174, and U.S. Pat. No. 8,145,316, all of which are incorporated herein by reference. In some approaches configured to induce selective damage to the renal nerves (renal denervation), manufacturers have developed and used radio frequency (RF) catheters, or drug delivery devices, which, while being minimally invasive, have tradeoffs in terms of ease of use, treatment accuracy, and regulatory complexity. An additional problem is that some patients may require a follow-up treatment with these treatments in cases where nerves are not adequately disrupted after receiving initial denervation therapy, and this introduces the complexity of having to apply multiple treatments over a period of time for the same condition.

Thus there is today an additional need to overcome the limitations and challenges of contemporary RF-based renal denervation therapy. RF contact requires energy transmission through contact with the targeted tissue. The manner of contact affects the intensity of RF energy transmission, wherein a smaller contact surface is desired to produce intensified tissue and nerve ablation. Once RF ablation has begun, tissue in the vicinity of a contact surface becomes desiccated as water molecules are induced into a vibrational state to the point of generating substantial heat within the tissue. An injury response is subsequently induced, and this has been shown to disrupt neural pathways passing through the zone of injury. However, some problems with contemporary RF methods for renal denervation are included in the list set forth here: (1) Renal artery bending motion may make accurate catheter-to-vessel contact difficult to reliably control, and therefore may make it difficult to control the degree and location of the desired RF-based injury; (2) Many point-based RF catheters only denervate a single contact point at a time, and cannot reliably guarantee the disruption of nerves around the entire renal artery circumference; (3) To accommodate problem no. 2, single point-based RF therapy has been developed, but this generally requires multiple ablations with targeted positions around the circumference of the renal artery; this is thought to increase the likelihood of disrupting the bundle of nerves passing by the renal artery; (4) If RF induced injury is too intensely localized within a short span of artery, there is a possibility of arterial occlusion or thrombosis.

In order to manage the above challenges, drug-driven therapies have been introduced to locally deliver chemical agents to induce injury to the renal nerves in the peri-adventitial space. However, these "combination device" therapies are costly and require extensive regulatory cost to facilitate approval.

Need in the Art

Thus, there is a need in the medical arts to produce a therapy which is relatively simple, accurate, effective, and/or requires less costly existing equipment and methods. The present invention addresses these and other needs.

SUMMARY OF THE INVENTION

In a preferred embodiment, the invention is a method for treating a human patient. The ailments from which the patient may suffer include but are not limited to myocardial infarction, heart failure, chronic renal failure, and hypertension. Initially, a span of renal artery is selected for implantation of a self-expanding stent. The artery has a first internal diameter, an artery wall, and is surrounded by peri-adventitial space through which at least one renal nerve extends. The first internal diameter is measured. Then, a self-expanding stent is selected. The selection is based on the requirement that the stent must be configured to be capable of expanding to have a second diameter that, in an expanded condition once implanted within the artery, is substantially greater than the first diameter. By "substantially greater" it is meant that, as a consequence of its oversize, the stent has sufficient expansive force to migrate through the artery wall, and into the peri-adventitial space. In some embodiments, the second diameter is at least 2 mm greater than the first diameter, in other embodiments, between 2 mm and 4 mm greater than the first diameter. In yet other embodiments, the second diameter is such as to be capable of expanding to be, in an expanded condition once implanted within the artery, between 10% and 20% greater than the first diameter.

Once an appropriate self-expanding stent is selected, it is implanted in the span of the renal artery, and is allowed to gradually expand to the second diameter, which it does by passing through the artery wall to become embedded in peri-advential space surrounding the artery. Once the stent is positioned within the peri-adventitial space its size is configured to apply disruptive forces to the renal nerve, to at least partially block the renal nerve or modulate a function of the renal nerve by applying pressure to the nerve with the stent.

In some embodiments, selecting a self-expanding stent includes selecting a self-expanding stent configured to have at least one strut with a width on an outer surface and a width on an inner surface, wherein the width on the outer surface is not more than 75% of the width on the inner surface.

In further embodiments, the invention further includes fragmenting the stent within the peri-advential space. This effect may be facilitated by forming at least one notch in the stent, the notch being configured to initiate crack propagation in the material forming the stent. In some embodiments, fragmenting the stent includes fragmenting the stent not less than 3 months after the implanting step, and not more than 6 months after the implanting step.

In other embodiments, the invention includes bioeroding the stent within the peri-adventitial space, and effecting this step may include bioeroding a polymer material that forms at least part of the stent. In some embodiments, the invention may include, after erosion of the stent, selecting a second self-expanding stent configured to be capable of expanding to have a third diameter that, in an expanded condition once implanted within the artery, is at least 2 mm greater than the first diameter, and then implanting the second stent in the span of the renal artery, whereby the second stent eventually expands to the third diameter and thereby passes through the artery wall to become embedded in peri-advential space surrounding the artery to at least partially block the renal nerve with the second stent.

In some embodiments, the invention may further include heating the stent within the peri-adventitial space. Such heating may be accomplished by heating the stent by magnetic resonance, and this in turn may be accomplished by inserting a source of magnetic resonance energy into the renal artery, adjacent the implanted stent. In other embodiments, heating may be accomplished by applying magnetic resonance energy from an energy source located outside the patient In other embodiments, heating may be accomplished by ultrasound and ultrasonic means, and this in turn may be accomplished by inserting a source of ultrasound energy into the renal artery, adjacent the implanted stent. In other embodiments, heating may be accomplished by applying ultrasound energy from a source located outside the patient.

In yet other embodiments, heating may be accomplished by RF signal induction, and this in turn by be accomplished by inserting a source of RF signal energy into the renal artery, adjacent the implanted stent. In other embodiments, it may be accomplished by applying a RF signal energy from a source located outside the patient.

In some embodiments, the invention may further include dissolving an agent from a surface of the stent into the peri-adventital space, and in some embodiments, the agent may be a neurotoxic agent.

DETAILED DESCRIPTION OF THE PREFERRED EMBODIMENTS

In conjunction with the figures, preferred embodiments having features of the invention are described. In one embodiment, the invention is a system and method for producing controlled damage to nerves surrounding a vessel which may be a vein or artery. As explained above, such damage, where appropriately carried out to the renal nerves, is configured to have an impact that imparts therapeutic effects to the body of a patient that outweigh the effects of the damage to the nerve itself.

Figure 1:
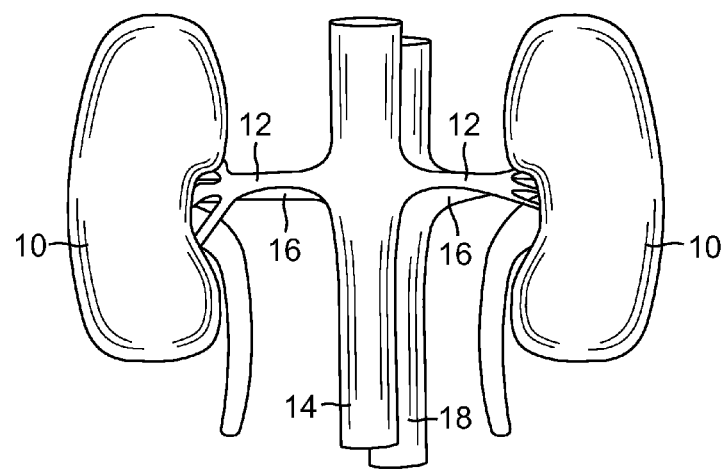
FIG. 1 is a schematic drawing of human anatomy showing a site that is suitable for implantation of an aggressively oversized stent having features of the present invention.

With reference to FIG. 1, the human renal anatomy includes kidneys 10 that are supplied with oxygenated blood by renal arteries 12, which are connected to the heart by the abdominal aorta 14. Deoxygenated blood flows from the kidneys to the heart via renal veins 16 and the inferior vena cava 18.

Figures 2, 3:
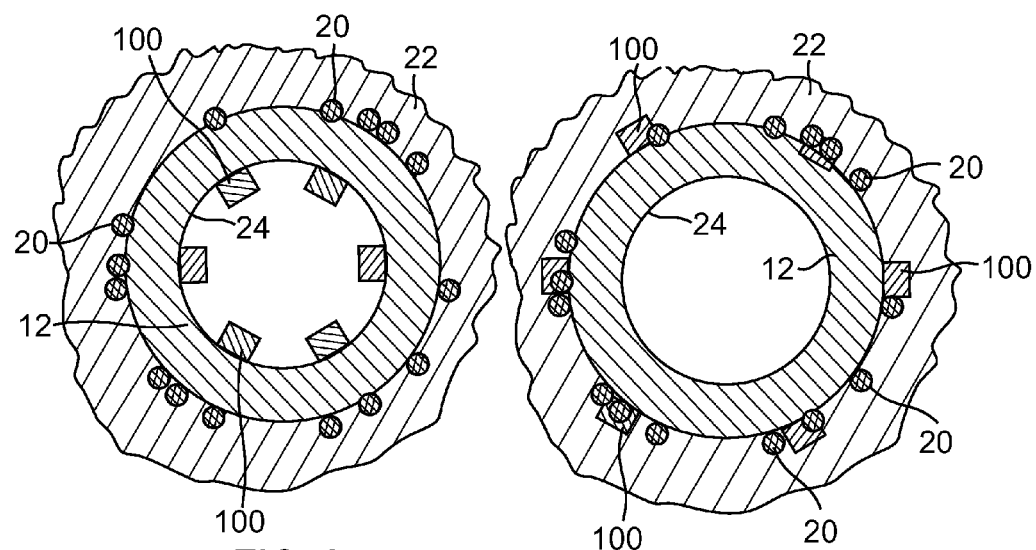
FIG. 2 is a schematic sectional view of an body lumen into which a stent having features of the present invention is implanted, and before the stent expands to pass through the wall of the lumen.
FIG. 3 is a schematic sectional view of the body lumen and stent in FIG. 2, showing the stent after it has migrated through the wall of the lumen.

FIG. 2 illustrates a sectional view through a renal artery. More specifically, the renal anatomy also includes renal nerves 20 extending longitudinally along the lengthwise dimension of renal artery 12 generally within the adventitia, or peri-adventitial space 22 (also referred to herein as peri-adventital tissue or adventitia), surrounding the artery 12.

In accordance with the principles of the invention, a novel device-driven therapy is presented to produce minimally invasive denervation for the purpose of hypertension management. The method of this embodiment presents a novel approach for disrupting sympathetic nerve function (denervation) by the implantation of an oversized and high-radial strength scaffold in the renal artery. With reference to the figures, it is disclosed how, to simplify treatment and manage the above mentioned tradeoffs, a novel inventive system and method is presented wherein a sufficiently high radial strength stent 100 is implanted in the renal artery 12 in a span of the artery surrounded by critical sympathetic nerves 20. This scaffolding stent is designed so that, when implanted, the stent has a substantial excess of chronic outward force. As a result, it is configured to encourage stent strut migration, over a period of time after implantation, through the arterial wall 24 and into the peri-adventitial space 22. This effect is demonstrated with reference to FIG. 2 and FIG. 3. FIG. 2 shows a sectional view of a self-expanding stent according to an embodiment of the invention, having just been implanted in the renal artery. FIG. 3 shows the same stent some weeks or months later, having migrated through the wall 24 of the renal artery, to a location within the peri-adventitial space. The known physical phenomenon by which the stent may migrate through the wall 24 into the pre-adventitial space 22 is described below. As exemplified in FIG. 3, some stent struts are in close contact with, and press up against, some renal nerves 20, thereby applying mechanical pressure on the nerve.

The simple presence of the struts of a stent so implanted and configured for migration into this nerve-rich region, when combined with kidney motion during breathing, is configured to bring denervating effect and disruption to the signals and function of those nerves 20 which are brought into contact with the stent. In a further embodiment of the invention, if further denervation is required after treatment, another scaffold may be implanted to induce further disruption to the nerves occupying the peri-adventitial space surrounding the renal artery.

Experimental Support for Feasibility of the Invention

The phenomenon by which stent struts of a substantially oversized stent pass through the vascular wall into peri-adventitial space surrounding the vessel has been well observed, and recorded in medical literature. It has been noted to occur within a period of a few months, typically from four to eight months. Following hereunder are summaries of two exemplary published references (incorporated herein by reference) which demonstrate that it is possible to safely design a stent (for example, a coil, weaved 'wallstent' style, or Nitinol tube-based stent) which is configured to penetrate through arterial intima and media and into the adventitia with good clinical outcomes:

Hong et al, Coronary Artery Disease. 1997 January: 8(1):45-8.—Acute And Chronic Effects Of Self-Expanding Nitinol Stents In Porcine Coronary Arteries. In this report, results are identified in which all of a number of self-expanding stents were successfully deployed, and remained patent acutely. Three undersized stents migrated proximally and there was one episode of subacute thrombosis in an oversized stent. The remaining stents were patent throughout the survival period and neointimal responses were favorable for up to six months. There was evidence of continuing stent expansion over time and the majority of stent struts had migrated into the adventitial space by six months. Re-endothelization occurred starting one week after implantation and was complete by eight weeks.

Von Birgelen et al, American Journal of Cardiology. 1998 Jul. 15; 82(2):129-34.—Coronary Wallstents show significant late, postprocedural expansion despite implantation with adjunct high-pressure balloon inflations. In this report it is recorded that adjunct high-pressure balloon inflations following the delivery of oversized self-expandable so-called Wallstents may affect their implied late, postprocedural self-expansion. Fifteen so-called Wallstents were examined, which were implanted following a strategy of stent oversizing and subsequent adjunct high-pressure balloon inflations. The excellent radiographic visibility of this stent permitted reliable quantitative coronary angiographic measurement of both lumen and stent dimensions before and after stenting, and at follow-up. At follow-up, the extent and distribution of in-stent neointimal proliferation were evaluated with volumetric intravascular ultrasound. Between post-intervention and follow-up examination, the mean stent diameter increased from 3.7+/−0.4 to 4.2+/−0.4 mm. It was found that, despite high-pressure implantation, the subject Wallstents showed significant late self-expansion, which resulted in larger stent dimensions at follow-up that assisted in accommodating in-stent neointimal proliferation. Conversely, late stent expansion had a significant relation to the extent of in-stent neointimal ingrowth.

Structure of Some Embodiments

Figure 4A:
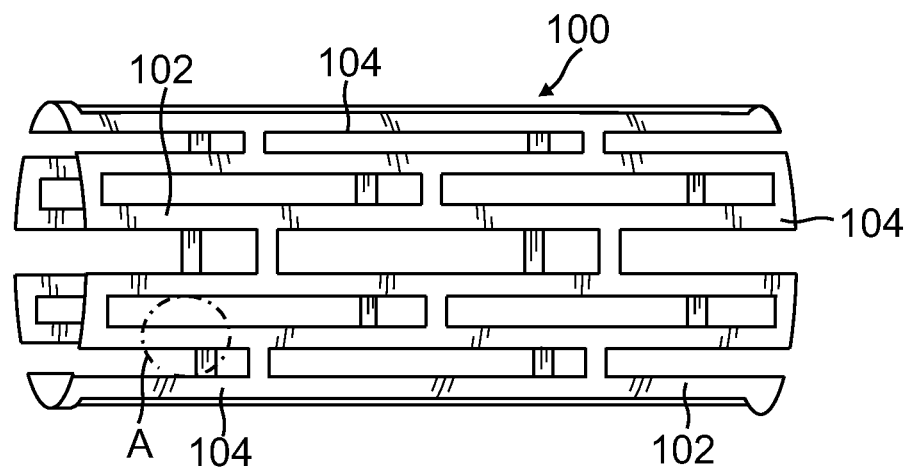
FIG. 4A is a perspective view of a stent having features according to the present invention.

In some embodiments for achieving the system and method of the invention, a self-expanding stent that may have a structure similar to that exemplified in FIG. 4A having features of the present invention is configured to include the use of a stent having sufficient self-expanding radial outward force to gradually pass through arterial tissue after deployment. Preferably, the stent's diameter is selected to be over-sized in relation to the vessel diameter into which it is to be implanted, and to have sufficient oversize ratio to enable a stent diameter that is about 2 mm, and in some embodiments between 2 mm and 4 mm larger than the arterial wall diameter after the stent has been implanted in the artery. In some embodiments, the stent will be formed from super elastic and/or shape-memory material. For example, in some embodiments, a Nitinol (Nickel-Titanium) stent may be used to accomplish the desired attributes. Increased radial strength may be accomplished through the use of substantial strut radial depth.

It will be appreciated that, in order to achieve a stent diameter that is larger than 2 mm (between 2 mm and 4 mm) outside the arterial wall after the stent has been implanted in the artery and migrated beyond the arterial wall, it will be necessary to select a stent that has a naturally expanded diameter (i.e. expanded without any constraint at all) which is even larger than the desired final implanted diameter. As will be appreciated by those of ordinary skill, this is because, even if the stent is selected to be aggressively oversized in relation to the artery it is to be implanted in, its final implanted diameter within the peri-adventitial space will be smaller than its naturally expanded diameter—due to the restraining forces applied by the vessel wall which will prevent the stent from reaching its full unrestrained diameter.

Figure 6:
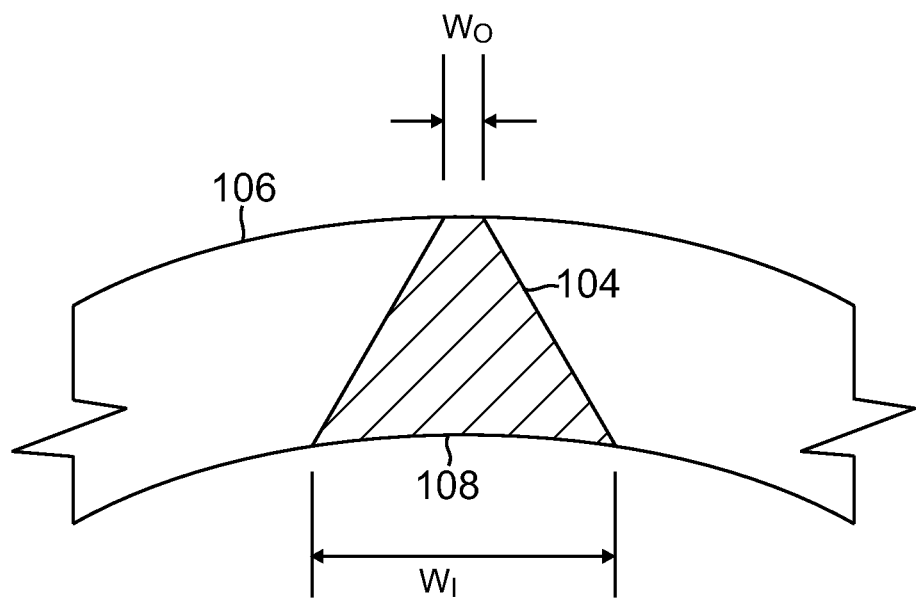
FIG. 6 is a detail view of an embodiment of the stent in FIG. 4A or FIG. 4B.

In some embodiments, struts 104 of the stent 100 may be shaped to facilitate migration, or enhance the degree of migration, through the wall of the vessel, and thence through the tissue surrounding the vessel into the peri-arterial space. In order to accomplish this result, struts 104 of the stent may be cut during manufacture to have a shape that presents a narrower edge width $W_O$ on the outside surface 106 of the stent than the edge width $W_I$ on the inside surface 108 of the stent, as is exemplified in FIG. 6. Cutting a stent to have this described shape may be accomplished by orienting a laser beam, configured to cut the stent during manufacture, along a non-radial path from the outside of the stent. It will be appreciated that maintaining a non-radial orientation of the laser beam will require a complex operation of repositioning the source of the laser beam, or having more than one laser beam source, but that such complexity may be reduced if the stent itself is configured to have a simple shape with a minimum of twists and turns, such as exemplified by the stent in FIG. 4A.

In some embodiments, the shape of the stent struts described above may be temporarily masked by a suitable soluble coating, designed to slowly dissolve in the arterial environment. Such a coating may be formed from known drug eluting compounds such as a rapamycin derivative drug. Such drugs are described in the application U.S. Ser. No. 13/789,473 which is currently co-owned herewith. Thus, in use, the stent may be initially delivered to a desired location with such a coating adhering to the stent struts. The coating has the result that a broader surface of the coated stent is presented to the arterial wall than would be presented by the surface of the naked strut alone. Then, as the coating slowly dissolves in the arterial environment, the shape of the naked struts as described above is exposed to the arterial wall, and the degree of migration process is speeded up due to the angled shape of the struts. In this way, the rate of migration into the arterial wall may be slowed initially by the presence of the coating, in order to allow the stent to settle into position. Once the coating has dissolved sufficiently, the rate of migration may accelerate to accomplish the objective of the invention.

Advantages

As will be apparent to those of ordinary skill, the system and method of the invention will provide the following advantages over presently used methods of neuromodulation. First, an oversized stent for aggressive expansion into the neo-intimal zone and beyond into the adventitial space of the renal artery will provide continuous circumferential nerve disruption or modulation around the renal artery. This feature overcomes the spatial problem inherent in the need to frequently reposition a point electrode or drug injection. The invention provides ease of delivery, with little or no additional substantial physician training required, especially for those already competent with renal artery stenting.

Fragmentation

Figure 4B:
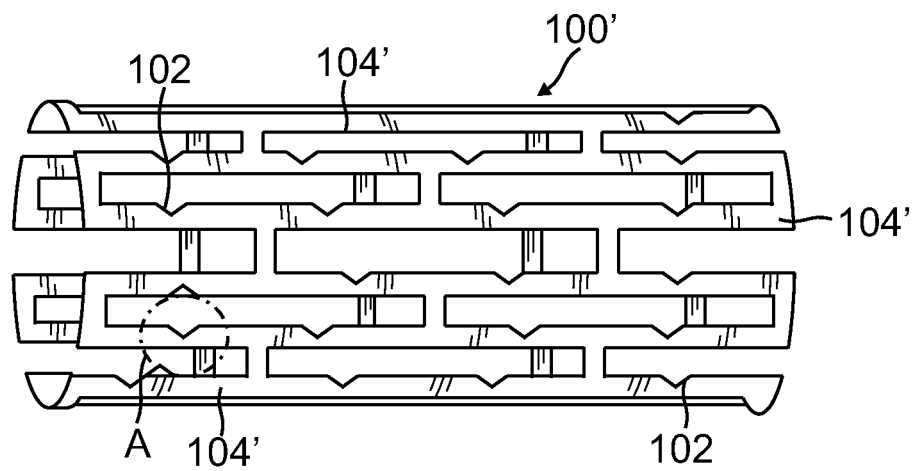
FIG. 4B is a perspective view of a stent having features according to another embodiment the invention.

In some embodiments of the invention, as exemplified in FIG. 4B, the implanted stent 100 may be designed with narrowed sections or notches 102 which are prone to fatigue failure in bending modes. These device fractures, which are configured to occur under excessive repeated bending modes associated with kidney motion due to inspiration and expiration, are configured to bring about exacerbated nerve disruption due to increased inflammation associated with independently movable strut motion. In this embodiment, the presence of fractured stent struts in the peri-adventitial space is configured to disrupt or modulate neural function by inducing sharpened pressure on the nerves and surrounding tissues, such sharpened pressure being applied by independently movable strut portions that have fractured and broken away from the original stent. Additionally, due to renal artery bending deformations associated with patient breathing cycles, the stent's broken struts are configured to repeatedly interact with nerves in the peri-adventitial space, thereby inducing cumulative injury or modulation and inflammation locally to the nerves surrounding the renal artery.

Figure 5:
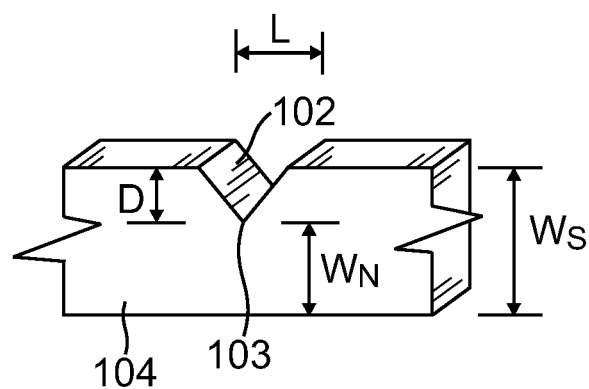
FIG. 5 is a detail view of a feature of the stent shown in FIG. 4B, taken from the area marked as "A."

Preferably, as exemplified in detail in FIG. 5, a narrowed section defines a notch 102 in the circumferential width of a strut 104 of the stent, the notch introducing a sharp corner 103 that is configured to provide a location of eventual stress fracture during bending through the known process of crack propagation. In some embodiments, the depth "D" of the notch, when material is removed from the width Ws of the strut, leaves a strut width Wn at the location of the notch which is in some embodiments about 50% of the strut width Ws. Each notch may have a length "L", as measured along the axial length of the stent. Moreover, a plurality of such notches 102 may be introduced into the struts along the length of the stent. Under this configuration, the strut at the location of the notch shall experience slight bending oscillations when positioned in the artery, and while the stent migrates through the wall of the artery, caused by the movement of the patient through inhalation and exhalation and other physical movement, such as may be caused by cardio vascular movement. The precise shape of a notch is preferably configured to increase the tendency of the strut at the location of at least some of the notches to fracture by fatigue failure in a timeframe after the stent has migrated through the wall of the artery. One of ordinary skill in the art would understand that the precise notch configuration required to produce this effect may be determined by experimentation, preferably by using a methodology including the following steps.

The following sets forth an exemplary experimental process by which an appropriate notch for the purpose may be configured. First, an assessment may be made of the amount of time required for the stent to pass through the wall of the artery and into the peri-adventitial space. It is believed that about six months is required for this process to take place. Next, the number, N, of bending oscillations that are likely to occur in this period may be determined. Assuming that inhalation and exhalation are the major causes of bending, it may be fair to assume that an inhalation to exhalation rate of ten cycles per minute is normal for an adult person. Thus, the designer of the stent would conclude that about 2.6 million cycles will take place in six months, and this number should be permitted to take place before fracture at the location of the notches becomes a probability. In other words, after 2.6 million cycles, the stent should have migrated through the artery wall and into the peri-adventitial space, and, after this timeframe, fracture would be desirable.

Then, it will be necessary for the designer to determine the magnitude of bending displacement that can be expected to occur in an average breathing cycle. An estimated movement of the stent within the artery may reasonably be assessed by affixing a known strain gauge system on a stent that is then implanted in an artery within an experimental canine subject, and measuring the strains and displacements that occur during a breathing cycle of the subject animal. For purposes of designing a stent under an embodiment of the present invention, such movement may reasonably be extrapolated to occur within a human subject.

Next, it will be necessary for the stent designer to conduct measurements to determine the shape of the notch in a strut that will be subjected to the anticipated fatigue loading. Having determined the displacement function that the stent may be expected to experience during the timeframe of being implanted in the subject human renal artery, a designer may apply to a notch of iteratively selected shape a fatigue test of known "S-N" variety, in which expected displacement is applied to a strut defining a notch, and measuring the number, "N," of cycles it takes to fracture the strut at the location of the notch. The designer may be obliged to iteratively alter the shape of the notch, giving it a more or less sharp angle, and/or a larger or smaller internal radius of curvature, and/or a greater or smaller width, until such time as the measured number "N" reaches the number estimated for fracture at the desired time—which is preferably six months under one embodiment of the invention. When the empirically determined number "N" which is associated with a particular notch configuration matches the estimated 2.6 million cycles in the course of iteratively altering the shape of the notch, a suitable shape for the notch may have been suitably identified. Having thus identified the shape of the notch, the designer may introduce this shape into a stent configured for implantation in a patient in order achieve the desired result.

Absorption

In yet a further embodiment of the invention, the scaffold struts of the oversize stent may be configured to be absorbed into the body of a patient in a time framework after substantial denervation has occurred. The configuration of material for bioabsorption after implantation in a patient is a field that has been developed to a relatively high degree of sophistication, as disclosed for example in U.S. Pat. No. 8,172,897, U.S. Pat. No. 7,875,283, and U.S. Pat. No. 7,956,100 which are incorporated herein by reference. As indicated by these and other prior art references, it is known in the art how to fabricate an implantable scaffold that will, after a period of time, experience bio-erosion and effectively dissolve entirely or substantially away from the location in which it has been implanted. Under the present embodiment of the invention in which an aggressively oversized scaffold is manufactured from bioerodable material, an advantage is provided in that, should the patient require further treatment by oversize scaffold after a first oversize stent scaffold has been implanted for renal denervation, a second implanted oversize scaffold migrating through the vessel wall will tend not to encounter a first implanted scaffold already in place, where it may otherwise interfere with and prevent the second scaffold from reaching the nerves surrounding the artery.

In application of the present embodiment, some metals are considered bioerodable since they tend to erode or corrode relatively rapidly when exposed to bodily fluids. Biostable metals refer to metals that are not bioerodable. Biostable metals have negligible erosion or corrosion rates when exposed to bodily fluids. In general, metal erosion or corrosion involves a chemical reaction between a metal surface and its environment. Erosion or corrosion in a wet environment, such as a vascular or peri-vascular environment, results in removal of metal atoms from the metal surface. The metal atoms at the surface lose electrons and become actively charged ions that leave the metal to form salts in solution. A bioerodable material suitable for use as a stent material are selected to form erosion products that do not negatively impact bodily functions.

Representative examples of biodegradable metals that may be used to fabricate an implantable medical device may include, but are not limited to, magnesium, zinc, and iron. In one embodiment of the invention, a bioerodable metal stent may be completely eroded when exposed to bodily fluids, such as blood, over a period of between about a week and about three months, or more narrowly, between about one month and about two months.

Representative examples of polymers that may be used to fabricate an implantable stent using the methods disclosed herein include, but are not limited to, poly(N-acetylglucosamine) (Chitin), Chitoson, poly(hydroxyvalerate), poly (lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATO-FINA Chemicals, Philadelphia, Pa.), ethylene-vinyl acetate copolymers, and polyethylene glycol.

In some embodiments, it may be desirable to manufacture an implantable stent that includes distinct regions that have different erosion profiles when exposed to bodily fluids. In this way the erosion profile of the stent may be customized to various treatments. Various embodiments of an implantable medical device with such erosion profiles may include a metallic region composed of a bioerodable metal, and a polymer region composed of a biodegradable polymer. The metallic region may be configured to erode at a different rate when exposed to bodily fluids than the polymer region when exposed to bodily fluids. In some embodiments, the polymer region may be configured to be an outer region or layer of the device and the metallic region may be an inner region or layer of the device. An outer region or layer may refer to a region or layer that is exposed first to a vascular environment. Direct contact or exposure of the inner region or layer to a vascular environment may be inhibited or prevented by an outer region or a region that is closer to the vascular environment. For example, a strut of a stent may include an inner region or core with an outer region or coating that inhibits or prevents direct contact or exposure of the inner region or core to a vascular environment. The metallic region may be configured to provide mechanical support for at least some of the time the device is implanted in a bodily lumen.

Fragmentation and Bioerosion

In some embodiments, the fragmentation process described above may be enabled in combination with the bioerosion process described above. In these embodiments a biostable coating, such as a teflon based compound, may be selectively applied to portions of a stent so as to leave other portions of the stent exposed to the moist environment of the peri-adventitial space. As a result of such selective coating, the exposed portions will be more prone to bioerosion than the coated portions. Thus, after a period of time, fragmentation of the stent at the uncoated portions will be accelerated in relation to the coated portions. This feature may be utilized to control the desired location of eventual fragmentation of the stent. Accordingly, by a strategic selection of portions to be coated or exposed, a stent such as that exemplified in FIGS. 7-9 may be constructed.

Figure 7:
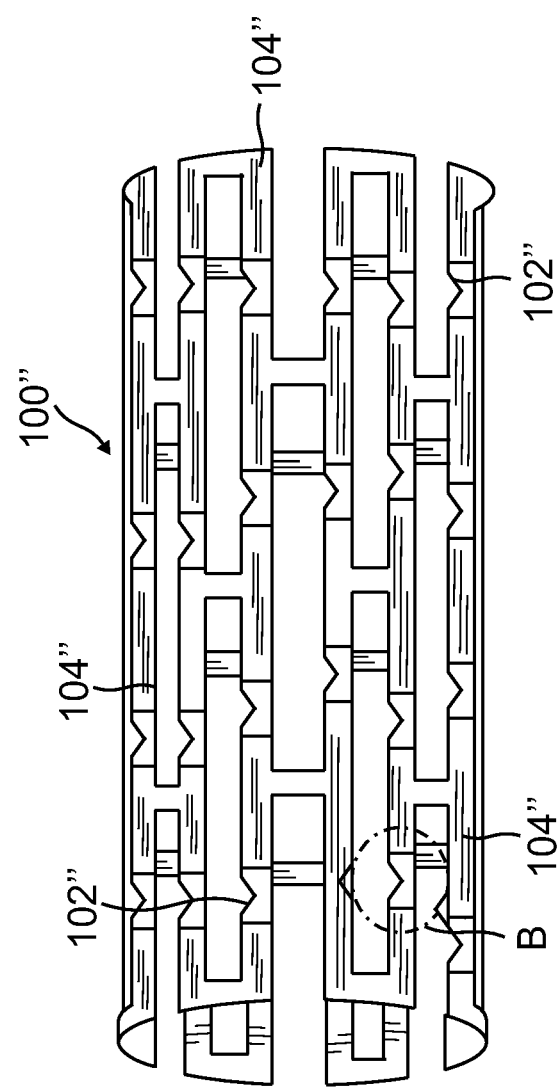
FIG. 7 is a perspective view of a stent having features according to another embodiment of the present invention.
Figure 8:
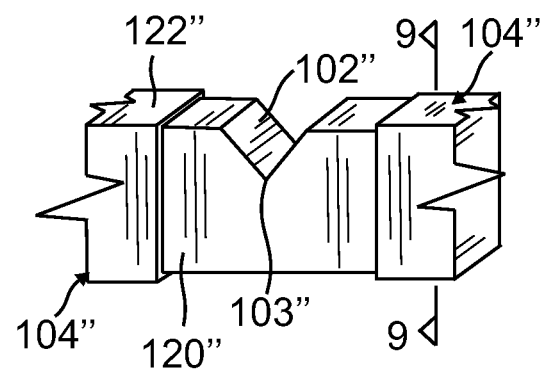
FIG. 8 is a detail view of a feature of the stent shown in FIG. 7, taken from the area marked as "B."
Figure 9:
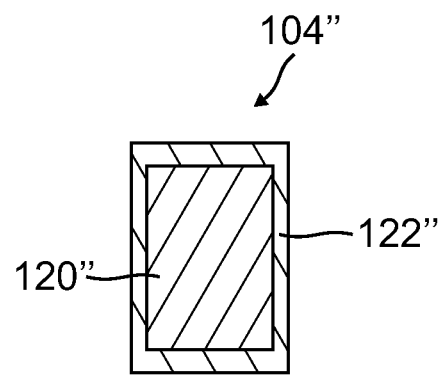
FIG. 9 is a sectional view taken substantially along the line marked 9-9 in FIG. 8.

FIG. 7 shows a schematic perspective view of a stent 100" having some of the features of the stent 100' seen in FIG. 4B. Similar to the stent 100' of FIG. 4B, the stent 100" of FIG. 7 has notches 102" cut into struts 104". These notches 102" are similarly designed to cause fragmentation of the stent 100" for the same reasons as set forth above. However, as best seen in FIGS. 8-9, in addition to the notches 102", stent 100" includes selectively located coating 122" which is configured to cover the metallic portion 120" of the struts 104" generally, but to be excluded from the area of the notches 102". The coating is designed to be biostable, and may include teflon compounds such as are known in the art when used to coat stents in their entirety.

In order to achieve selective coating of the stent with the coating 120", the stent may be manufactured as follows. After the stent has been cut from its initial tubular form, a small amount of an inert liquid wax like material such as paraffin wax may be applied to the region of the stent that includes the notch 120", or other area selected to eventually have no coating. After this process is complete, the entire stent may be coated with the selected biostable coating such as teflon based compound. Then, the coated stent may be placed in a heated fluid environment, preferably gaseous, until the stent is heated and the wax like material melts. At this point, a jet of fluid may be directed at the stent, to remove the coating which will be attached to the liquid wax. The net result is a stent which is coated over the majority of the strut area, but which is exposed in selected regions. It will be appreciated that in addition to selecting a notch region to receive no coating, other regions also may be selected to have no coating, according to specific design needs. The final result is a stent that is configured to fragment once it is implanted in the moist per-adventitial space, wherein the fragmentation commences in regions which are not coated with biostable coating, and which may, additionally be provided with notches to initiate crack propagation.

Heating

In other embodiments of the invention, once the aggressively oversized scaffold or stent has migrated to a desired extent through a vessel wall of a patient where it is positioned adjacent renal nerves, the scaffold may be heated by means known in the art such as induction heating by magnetic resonance, by ultrasound, or by RF signal induction. By heating the scaffold, additional denervation is applied to the nerves to provide the beneficial effects described herein.

The art of heating metal implants in a patient's body is a field that has been developed to some relatively high degree of sophistication, as disclosed for example in U.S. Pat. No. 6,786,904 (magnetic resonance), U.S. Pat. No. 6,451,044 (ultrasound), U.S. Pat. No. 6,238,421 (RF signal induction)—all of which are incorporated herein by reference. These, or similar, methods may be used in conjunction with the oversize scaffold of the present invention, and denervation that takes place due to mechanical interference with the nerves can, in addition, be enhanced by heating the nerves to further advance denervation.

Where magnetic resonance is to be used, the induction heating process may be carried out with a heating system as follows. The patient may be placed horizontally beneath a sending antenna configured to generate a magnetic field. Magnetic energy may be generated by a generator and amplifier unit, and electrical current is caused to flow to a resonant circuit which is preferably positioned close to the energy sending antenna. For the present purpose, the frequency range is preferably between 100 kHz and 900 kHz. During the inductive heating process, electric energy is transmitted to the metal stent by the magnetic field, which by the means of an induction coil flowing alternating current produces a magnetic alternating field, which consequently induces a certain current in the responsive metal stent. The electric energy supplied by the induction coil is first converted into magnetic energy, which is then converted into heat energy in the stent. The current density in the stent is determined through the so-called skin-effect. The highest current density is reached at the stent surface. The current density drops off inside the stent rapidly. This has the advantageous effect of localizing heat gain in the stent at the stent surface, where there is contact with the body tissue including renal nerves.

A suitable material for an oversized stent according to the principles of the present invention that can be effectively warmed by induction is, in some embodiments, an alloy of nickel and iron wherein the ratio of nickel to iron is selected to result in a magnetic permeability that generates the desired amount of heat in the spatial environment under which the system is configured to operate. In other embodiments, the stent may be formed from nickel-copper alloys, Nickel Palladium alloys, Palladium Cobalt alloys, and Nickel-Silicon alloys, where the ratio of metals in the alloys are selected according to the same principle.

Drug Elution

In yet a further embodiment of the invention, the oversize scaffold may be configured so that, once it has migrated to a desired extent through a vessel wall of a patient where it is positioned adjacent renal nerves, the scaffold elutes known neurotoxic drugs which are taken up by the renal nerves to cause denervation. The art of injecting neurotoxic drugs into a patient's body for purposes of neuromudulation is a field that has been developed to a relatively high degree of sophistication, as disclosed for example in U.S. Pat. No. 7,162,303. Furthermore, the art of fabricating stents that will elute therapeutic drugs into a patient's vascular system and related tissue has also been developed, as disclosed for example in U.S. Pat. No. 7,807,722 and U.S. Pat. No. 8,187,322 which are incorporated herein by reference. These, or similar methods may be used in conjunction with the oversize scaffold of the present invention, and denervation that takes place due to mechanical interference within the nerves can be enhanced by, in addition, application of neurotoxic agents by elution from the implanted stent.

Thus, the embodiments described provide an advantageous system and method for stimulating and blocking renal nerves, and thereby providing a therapeutic result for patients suffering from ailments including acute myocardial infarction, heart failure, chronic renal failure and hypertension. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A method for treating a patient diagnosed with a cardio-renal disease or disorder, the method comprising:
   a. selecting a span of a renal artery in the patient for implantation of a self-expanding stent, the renal artery having a first internal diameter, an artery wall, and being surrounded by a peri-adventitial space through which at least one renal nerve extends;
   b. measuring the first internal diameter;
   c. selecting a self-expanding stent having a cylindrical outer surface, the stent being configured to have a first external diameter in an unexpanded condition and being capable of expanding to have a second external diameter, wherein the second external diameter once the stent is implanted within the artery, is larger than the first internal diameter;
   d. implanting the stent in the span of the renal artery, whereby the stent eventually expands towards the second external diameter and thereby passes through the artery wall to become embedded in the peri-adventitial space surrounding the artery; and
   e. applying pressure to the at least one renal nerve with the stent, thereby at least partially modulating a function of the at least one renal nerve; and
   f. heating the stent within the peri-adventitial space with an external heating source located outside of the patient.

2. The method of claim 1, wherein heating the stent includes heating the stent by ultrasound.

3. The method of claim 2, wherein heating the stent by ultrasound includes inserting a source of ultrasound energy into the renal artery, adjacent the stent.

4. The method of claim 2, wherein heating the stent by ultrasound includes applying a source of magnetic resonance energy located outside the patient.

5. The method of claim 1, wherein heating the stent includes heating the stent by magnetic resonance.

6. The method of claim 5, wherein heating the stent by magnetic resonance includes inserting a source of magnetic resonance energy into the renal artery, adjacent the stent.

7. The method of claim 5, wherein heating the stent by magnetic resonance includes applying a source of magnetic resonance energy located outside the patient.

8. The method of claim 1, wherein heating the stent includes heating the stent by Radio Frequency signal induction.

9. The method of claim 8, wherein heating the stent by Radio Frequency signal induction includes inserting a source of Radio Frequency signal energy into the renal artery, adjacent the implanted stent.

10. The method of claim 8, wherein heating the stent by Radio Frequency signal induction includes applying a source of Radio Frequency signal energy located outside the patient.

11. A method for treating a patient diagnosed with a cardio-renal disease or disorder, the method comprising:
   a. selecting a span of a renal artery in the patient for implantation of a self-expanding stent, the renal artery having a first internal diameter, an artery wall, and being surrounded by a peri-adventitial space through which at least one renal nerve extends;
   b. measuring the first internal diameter;
   c. selecting a self-expanding stent having a cylindrical outer surface, the stent being configured to have a first external diameter in an unexpanded condition and being capable of expanding to have a second external diameter, wherein the second external diameter once the stent is implanted within the artery, is larger than the first internal diameter;
   d. implanting the stent in the span of the renal artery, whereby the stent eventually expands towards the second external diameter and thereby passes through the artery wall to become embedded in the peri-adventitial space surrounding the artery; and
   e. applying pressure to the at least one renal nerve with the stent, thereby at least partially modulating a function of the at least one renal nerve;
   f. fragmenting the stent within the peri-adventitial space, wherein fragmenting the stent includes forming at least one notch in the stent prior to implanting the stent, the at least one notch being configured to initiate crack propagation.

12. The method of claim 11, wherein fragmenting the stent includes applying a biostable coating to a first selected portion of the stent, and excluding the biostable coating from a second selected portion of the stent that includes the notch.

\* \* \* \* \*